United States Patent [19]

Fergason

[11] Patent Number: 5,113,271
[45] Date of Patent: * May 12, 1992

[54] LIGHT BLOCKING AND VISION RESTORATION APPARATUS WITH GLINT CONTROL

[76] Inventor: James L. Fergason, 92 Adam Way, Atherton, Calif. 94025

[*] Notice: The portion of the term of this patent subsequent to Jan. 29, 2008 has been disclaimed.

[21] Appl. No.: 646,160

[22] Filed: Jan. 25, 1991

Related U.S. Application Data

[63] Continuation of Ser. No. 230,622, Aug. 10, 1988, Pat. No. 4,988,167.

[51] Int. Cl.[5] .................................. G02F 1/133
[52] U.S. Cl. ........................... 359/38; 359/51; 359/63; 359/70; 359/94
[58] Field of Search .............. 350/337, 338, 339 F, 350/347 E, 347 V, 384, 389, 390, 391; 359/63, 70, 68, 94, 93, 51, 38

[56] References Cited

U.S. PATENT DOCUMENTS

| Re. 32,521 | 10/1987 | Fergason | 350/347 E |
|---|---|---|---|
| 4,232,948 | 11/1980 | Sharks | 350/347 R |
| 4,239,349 | 12/1980 | Scheffer | 350/347 R |
| 4,279,474 | 7/1981 | Belgorod | 359/41 |
| 4,385,806 | 5/1983 | Fergason | 359/63 |
| 4,435,047 | 3/1984 | Fergason | 350/347 V |
| 4,436,376 | 3/1984 | Fergason | 350/347 E |
| 4,444,469 | 4/1984 | Kaye | 359/63 |
| 4,462,661 | 7/1984 | Witt | 359/40 |
| 4,465,969 | 8/1984 | Tada et al. | 350/390 |
| 4,540,243 | 9/1985 | Fergason | 350/347 E |
| 4,541,691 | 9/1985 | Buzak | 350/347 R |
| 4,606,611 | 8/1986 | Fergason | 350/345 |
| 4,674,841 | 6/1987 | Buzak | 350/347 R |
| 4,765,719 | 8/1988 | Fergason | 350/347 V |
| 4,988,167 | 1/1991 | Fergason | 359/63 |

Primary Examiner—Stanley D. Miller
Assistant Examiner—Anita Pellman Gross
Attorney, Agent, or Firm—Renner, Otto, Boisselle & Sklar

[57] ABSTRACT

According to one aspect of the invention, a system for controlling light, includes (1) apparatus for responding to incident electromagnetic radiation, including a first medium through which incident electromagnetic radiation may be transmitted; liquid crystal means positioned with respect to said first medium for responding to a characteristic of the incident electromagnetic radiation to cooperate with such first medium to effect refraction of such electromagnetic radiation at an interface of said first medium and said liquid crystal means; and (2) apparatus for filtering a wavelength of light, including a variable polarization rotator means for supplying input light at a prescribed angle of polarization, variable dispersion means for rotating the plane of polarization of such input light an amount that is a function of the wavelength of such input light, and analyzer means for blocking transmission of that light which is output by said variable dispersion means and has a plane of polarization which is crossed relative to the axis of polarization of said analyzer means. The invention also may include a glint reducing device.

26 Claims, 1 Drawing Sheet

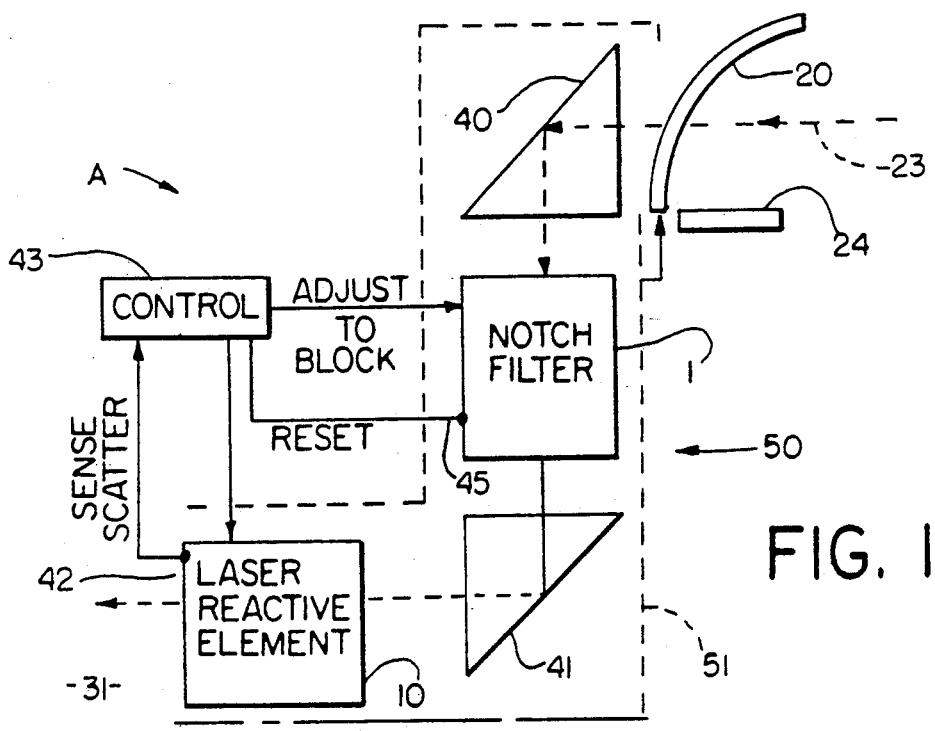
FIG. 1
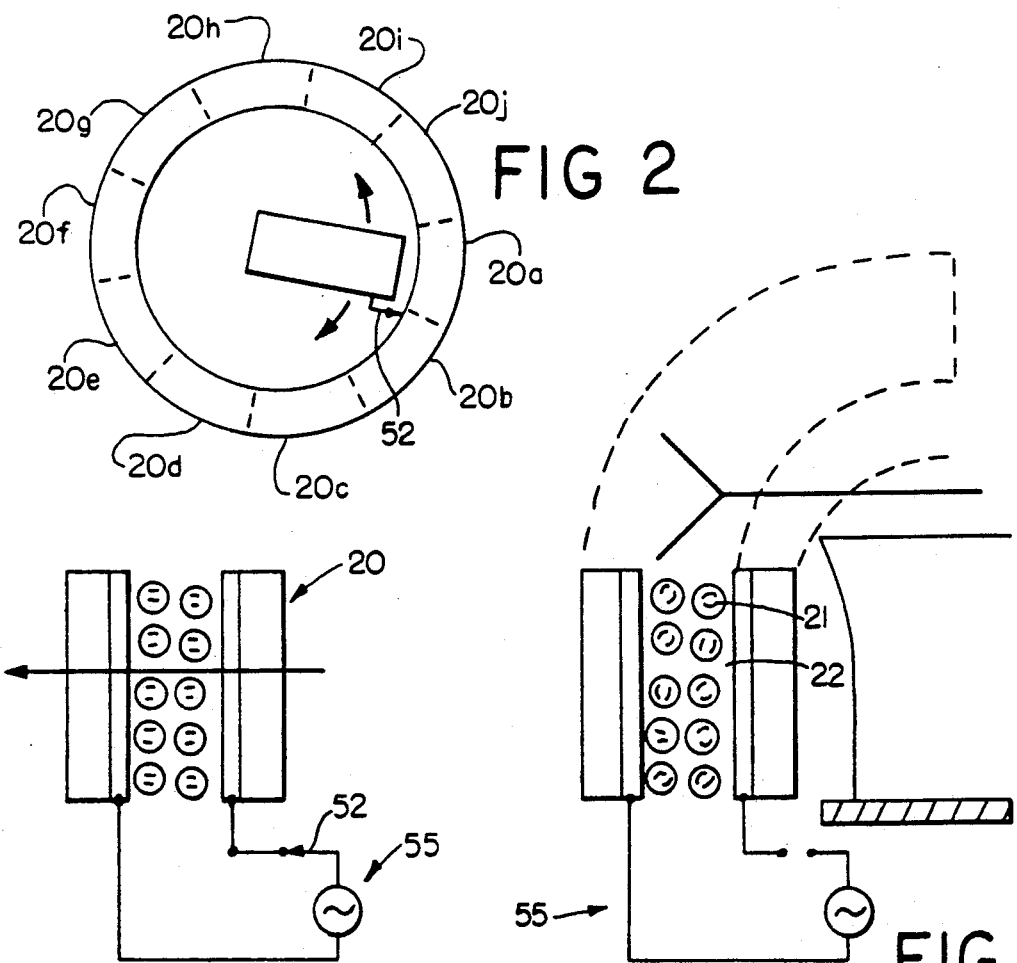
FIG 2
FIG. 3
FIG. 4

LIGHT BLOCKING AND VISION RESTORATION APPARATUS WITH GLINT CONTROL

This is a continuation of copending application Ser. No. 07/230,622 filed on Aug. 10, 1988 now U.S. Pat. No. 4,988,167.

TECHNICAL FIELD

This invention relates to light blocking devices to protect the eyes or other object from specific electromagnetic energy, such as laser light, and to means for restoring vision after termination of or blocking of an undesirable light component. The invention also relates to a glint control device to avoid undesirable light reflections.

The invention is described with respect to electromagnetic energy that is in the visible, ultraviolet and infrared wavelength or frequency spectrum. Such electromagnetic energy will be referred to for convenience as light. It will be appreciated that features of the invention may be used in connection with electromagnetic radiation in other spectra.

CROSS-REFERENCE TO RELATED PATENTS AND APPLICATIONS

Reference is made to applicant's U.S. Pat. Nos. 4,435,047 and 4,606,611. Reference also is made to applicant's pending U.S. patent application Ser. No. 010,748, filed Feb. 4, 1987 for Optical Protection Using Smectic Liquid Crystal. Further, reference is made to applicant's concurrently filed U.S. patent applications Ser. No. 230,789 for SYSTEM FOR CONTINUOUSLY ROTATING PLANE OF POLARIZED, LIGHT AND APPARATUS USING THE SAME, and Ser. No. 230,790 for DYNAMIC OPTICAL NOTCH FILTER. The entire disclosures of the above patents and applications are hereby incorporated by reference.

BACKGROUND

In the field of eye protection disclosure of the above '748 application provides for blocking of direct transmission of light to a person to protect the eyes from intense radiation or the like. Such blocking is effected by causing a scattering of light due to index of refraction considerations brought about automatically in response to the input of a prescribed radiation to the device. Since the light/radiation is scattered, the intensity thereof is significantly reduced. After the intense radiation condition is alleviated, the device can be re-set to transmit light and images carried thereby by applying appropriate electrical and/or temperature inputs to the device. The device relies on smectic liquid crystal material and Kerr effect occurring therein to defocus light with respect to curved surfaces within which the liquid crystal is contained or with respect to which the liquid crystal is positioned. The device is generally insensitive to wavelength.

Scattering of light in response to a mismatch of index of refraction between liquid crystal material and a containment medium is disclosed in two first-mentioned patents above. Transmission of such light will occur in response to a prescribed input, such as an electric field or a magnetic field. The devices disclosed in such patents utilize nematic curvilinearly aligned phase liquid, which preferably has positive dielectric anisotropy and an ordinary index of refraction that is matched to the containment medium so as to minimize scattering when the liquid crystal is aligned with respect to an electric field, for example. The liquid crystal also has an extraordinary index of refraction that is different from the index of refraction of the containment medium; therefore, in the absence of an electric field, for example, the liquid crystal, which assumes a somewhat curvilinear alignment, and the containment medium tend to scatter light.

The relationships of certain optical components for affecting light, particularly polarized light, is described, for example, in Jenkins and White, FUNDAMENTALS OF OPTICS, McGraw-Hill Book Company, New York, 1957. For example, at Chapter 27 of such text, the interference of polarized light is described. Polarized light and use of various optical components with polarized light also are described elsewhere in such text. The entire disclosure of such text is incorporated herein by reference.

A liquid crystal device for phase modulating polarized light is disclosed in U.S. Pat. Nos. 4,385,806, 4,436,376, 4,540,243, and Re. 32,521. The disclosures of such patents hereby are incorporated by reference. In such device linearly polarized light is phase-modulated as such light passes through a liquid crystal cell to which a modulated electrical carrier wave signal is applied as an electrical potential to develop an electric field across the liquid crystal material affecting alignment of the liquid crystal structure therein. The light which is transmitted through the liquid crystal cell is phase modulated as a function of the modulated electrical carrier wave signal. More specifically, the liquid crystal cell effectively separates the incident linearly polarized light into the quadrature components, i.e., the ordinary and extraordinary rays, thereof, and effects a retardation of one ray or component relative to the other as the light is transmitted through the cell. The amount of retardation, i.e., the effective optical thickness of the liquid crystal cell, is a function of the modulated electrical carrier wave signal. The liquid crystal cell disclosed in such patents utilizes a so-called surface mode switching technique which is fast acting, e.g., for example providing switching response times of as little as 10 to 100 microseconds.

In the variable rotator patent application mentioned above, an apparatus for rotating polarization of polarized light, includes a source of linearly polarized input light or a means to effect linear polarization of input light, a variable retarder that retards the phase of one quadrature component of such linearly polarized input light an amount relative to the phase of the other quadrature component, and an analyzer that converts the quadrature components from the variable retarder to linearly polarized light that has a plane of polarization which is a function of the amount of such phase retardation. The variable retarder is a liquid crystal cell that operates according to surface mode alignment and switching characteristics in response to electric field input to alter the relative retardation or phase separation of the ordinary and extraordinary ray components of incident light. Such liquid crystal cell is disclosed in the aforementioned U.S. patents.

In the notch filter patent application mentioned above, there is disclosed an apparatus for filtering a wavelength of light, including a variable polarization rotator for supplying input light as polarized light at a prescribed angle of polarization, a variable dispersion device for rotating the angle or plane of polarization of such input light an amount that is a function of the wavelength of such input light, and an analyzer for blocking transmission of that light which is output by said variable dispersion device and has a plane or angle of polarization which is crossed relative to the axis of polarization of such analyzer. The apparatus for rotating polarization is that of the variable rotator patent. An example of a wavelength dependent optical dispersion device is a liquid crystal cell with parallel plate walls, e.g., of glass, with a quantity of cholesteric liquid crystal between the walls.

BRIEF SUMMARY OF THE INVENTION

According to one aspect of the invention, a system for controlling light, includes (1) apparatus for responding to incident electromagnetic radiation, including a first medium through which incident electromagnetic radiation may be transmitted; liquid crystal means positioned with respect to said first medium for responding to a characteristic of the incident electromagnetic radiation to cooperate with such first medium to effect refraction of such electromagnetic radiation at an interface of said first medium and said liquid crystal means; and (2) apparatus for filtering a wavelength of light, including a variable polarization rotator means for supplying input light at a prescribed angle of polarization, variable dispersion means for rotating the plane of polarization of such input light an amount that is a function of the wavelength of such input light, and analyzer means for blocking transmission of that light which is output by said variable dispersion means and has a plane of polarization which is crossed relative to the axis of polarization of said analyzer means.

Another aspect of the invention relates to a glint reducing system, including an elliptically shaped variable reflector, an absorber for receiving light reflected by the reflector to avoid producing spurious glint reflectors, said variable reflector comprising liquid crystal material in a containment medium, the liquid crystal having an ordinary index of refraction matched to that of the containment medium to transmit light without substantial scattering and an extraordinary index of refraction different from that of the containment medium to cause scattering of light and reflection toward said absorber, and input means for applying a prescribed input to said liquid crystal to switch the same between modes presenting ordinary or extraordinary index of refraction characteristics to incident light, thereby selectively to permit light transmission or to reflect light toward said absorber.

These and other objects, advantages and features of the invention will become more apparent as the following detailed description proceeds. It will be appreciated, though, that the scope of the invention is to be determined by the scope of the claims and the equivalents thereof.

To the accomplishment of the foregoing and related ends, the invention, then, comprises the features hereinafter fully described in the specification and particularly pointed out in the claims, the following description and the annexed drawings setting forth in detail certain illustrative embodiments of the invention, these being indicative, however, of but several of the various ways in which the principles of the invention may be employed.

BRIEF DESCRIPTION OF THE DRAWINGS

In the annexed drawings:

FIG. 1 is a schematic side elevation view of the apparatus of the invention;

FIG. 2 is a fragmentary top view of the apparatus of FIG. 1; and

FIGS. 3 and 4 are schematic side elevation views of the glint reducing device of the invention, respectively in light transmitting and light blocking modes.

DESCRIPTION OF THE PREFERRED EMBODIMENT

Referring in detail to the drawings, wherein like reference numerals designate like parts in the several figures, and initially to FIG. 1, a light blocking and vision restoration apparatus with glint control in accordance with the invention is designated A. The apparatus A includes an a dynamic notch filter 1, which may be the same as the dynamic notch filter disclosed in the corresponding above-identified patent application. Such filter 1 functions to block transmission of a prescribed wavelength of light. For a further description of the dynamic notch filter reference is made to the mentioned application.

The system A also includes a laser reactive element 10, which responds quickly to a incident light in excess of a predetermined magnitude to block direct transmission of such light, e.g. by scattering some of the light preventing transmission. Such element 10 may be, for example, a liquid crystal material operative to undergo Kerr effect in response to and proportionally to the intensity of incident light in excess of a predetermined magnitude, and a medium having a different index of refraction than the liquid crystal material when the latter is undergoing Kerr effect, the index of refraction of the liquid crystal material increasing in response to Kerr effect and being cooperative with said further medium to cause self focusing to defocus and/or to decollimate incident light.

The element 10 is disclosed in detail in applicant's above-mentioned '748 application.

As is seen in FIG. 1, the system A also includes a glint reducing device 20. The glint reducing device is a curved, e.g. elliptical, film of nematic liquid crystal 21 in a containment medium 22, e.g., as is disclosed in applicant's two first-mentioned patents above. In the absence of a prescribed input to the device 20, which is illustrated schematically in FIGS. 3 and 4, incident light 23 is scattered and is directed toward a absorber 24. Such scattering is due to scattering at the reflection at, the surface and due to scattering as a result of mismatch of indices of refraction of the liquid crystal and the containment medium. Light would be transmitted through the device 20 when electric field, for example, is applied thereto, to align the liquid crystal so that the index of refraction thereof is matched to that of the containment medium. A full description of such nematic curvilinear aligned phase type of liquid crystal device is presented in applicant's two first-mentioned patents.

As is seen in FIG. 3, when a field is applied, the glint reducing device 20 transmits light 23 for delivery through the notch filter 1 and the laser reactive element 10 for viewing at 31. In FIG. 4, the glint reducing device is scattering, blocks transmission of light and reflects light to the absorber 24.

Referring to FIG. 1, the incident light 23 on the glint reducer is reflected by the prism reflector 40 to the notch filter. Moreover, light transmitted through the notch filter is reflected by a further prism reflector 41 to the laser reactive element 10. The light can be viewed at 31.

If the incident light contains a component that has an intensity that causes the laser reactive element 10 to go into scattering mode, such mode may be detected by a detector 42, which sends a signal to a control device 43, such as a computer, indicating such scattering mode. Preferably the control 43 then signals the notch filter to adjust to block transmission of the wavelength of light that is causing the extreme condition which caused the laser reactive element to go into scattering mode. Such input to the notch filter may be one that simply causes the notch filter to block a prescribed expected wavelength. Alternatively, sensor means may be provided, e.g. in the form of a further sensor 45, to determine whether the wavelength that had produced the extreme condition had been blocked. Upon detecting such blocking, the sensor 45 would indicate the same to the control 43, which in turn would re-set the laser reactive element 10 to transmit light.

The system A may be in the form of a periscope type device 50, e.g., contained in a housing 51. The housing 51 may be rotated to view through various portions of the circular glint reducing device 20. Moreover, the glint reducing device may include plural segments 20a, 20b, etc., which may be contacted by a contact 52 that is movable with the housing as the latter is rotated to view out of such segments. Connection of the contact 52 with a respective segment will cause electrical input to such segment from the circuit 55 shown in FIGS. 3 and 4, to cause the segment to be transparent for viewing. In the meantime, the other segments are scattering and are relatively low in glint and minimize viewing from a outside person or source.

I claim:

1. A system for controlling electromagnetic radiation comprising:
   a medium through which electromagnetic radiation may be transmitted;
   means positioned with respect to said medium for defocusing and/or decollimating said electromagnetic radiation passing through said medium which has an intensity in excess of a predetermined magnitude;
   means for filtering said electromagnetic radiation having an intensity in excess of said predetermined magnitude; and
   control means for activating said means for filtering in the event said means for defocusing and/or decollimating is in a scattering mode.

2. The system of claim 1, wherein said means for defocusing and/or decollimating comprises liquid crystal means positioned with respect to said medium for responding to a characteristic of said electromagnetic radiation to cooperate with said medium to effect refraction of said electromagnetic radiation at an interface of said medium and said liquid crystal means.

3. The system of claim 2, wherein said liquid crystal means comprises liquid crystal material operative to undergo Kerr effect in response to and proportionally to the intensity of said electromagnetic radiation in excess of said predetermined magnitude, said medium having a different index of refraction than the liquid crystal material when the latter is undergoing Kerr effect, and wherein said index of refraction of the liquid crystal material increases in response to Kerr effect and cooperates with said medium to cause said scattering.

4. The system of claim 1, wherein said means for filtering comprises a variable polarization rotator means for supplying input electromagnetic radiation at a prescribed angle of polarization, variable dispersion means for rotating the plane of polarization of such input electromagnetic radiation an amount that is a function of the wavelength of such input electromagnetic radiation, and analyzer means for blocking transmission of that electromagnetic radiation which is output by said variable dispersion means and has a plane of polarization which is crossed relative to the axis of polarization of said analyzer means.

5. The system of claim 1, wherein said control means comprises a computer.

6. The system of claim 5, wherein said control means further comprises detector means for detecting said scattering mode.

7. The system of claim 6, wherein said control means causes said means for filtering to block transmission of the wavelength of said electromagnetic radiation having an intensity in excess of said predetermined magnitude.

8. The system of claim 7, wherein said control means further comprises a sensor to detect whether said transmission of said wavelength has been blocked.

9. The system of claim 8, wherein said means for defocusing and/or decollimating comprises liquid crystal means positioned with respect to said medium for responding to a characteristic of said electromagnetic radiation to cooperate with said medium to effect refraction of such electromagnetic radiation at an interface of said medium and said liquid crystal means, and wherein said control means functions to reset said means for defocusing and/or decollimating to permit transmission of non-filtered wavelengths of said electromagnetic radiation upon detecting that said wavelength has been blocked by said means for filtering.

10. The system of claim 6, wherein said control means causes said means for filtering to block a prescribed wavelength.

11. The system of claim 1, further comprising glint reducing means for reducing glint reflections at a location where said electromagnetic radiation enters said medium.

12. The system of claim 11, wherein said glint reducing means comprises an elliptically shaped variable reflector, an absorber for receiving electromagnetic radiation reflected by the reflector to avoid producing spurious glint reflections, said variable reflector comprising liquid crystal material in a containment medium, the liquid crystal having an ordinary index of refraction matched to that of the containment medium to transmit said electromagnetic radiation without substantial scattering and an extraordinary index of refraction different from that of the containment medium to cause scattering of said electromagnetic radiation and reflection toward said absorber, and input means for applying a prescribed input to said liquid crystal to switch the same between modes presenting ordinary or extraordinary index of refraction characteristics to said electromagnetic radiation, thereby selectively to permit transmission of said electromagnetic radiation or to reflect said electromagnetic radiation toward said absorber.

13. The system of claim 12, said reflector being oriented in a circle and having plural segments that can be selectively made transmitting or reflecting.

14. A system for controlling electromagnetic radiation, comprising:

an apparatus for responding to electromagnetic radiation, during
a medium through which said electromagnetic radiation may be transmitted;
liquid crystal means positioned with respect to said medium for responding to a characteristic of said electromagnetic radiation to cooperate with said medium to effect refraction of said electromagnetic radiation at an interface of said medium and said liquid crystal means;
a filtering apparatus for filtering a wavelength of said electromagnetic radiation, including a variable polarization rotator means for supplying input electromagnetic radiation at a prescribed angle of polarization, variable dispersion means for rotating the plane of polarization of such input electromagnetic radiation an amount that is a function of the wavelength of such input electromagnetic radiation, and analyzer means for blocking transmission of that electromagnetic radiation which is output by said variable dispersion means and has a plane of polarization which is crossed relative to the axis of polarization of said analyzer means; and
control means for activating said filtering apparatus upon said liquid crystal means responding to said characteristic of said electromagnetic radiation.

15. The system of claim 14, wherein said control means comprises a computer.

16. The system of claim 14, further comprising glint reducing means for reducing glint reflections at a location where said electromagnetic radiation enters said medium.

17. The system of claim 16, wherein said glint reducing means comprises an elliptically shaped variable reflector, an absorber for receiving said electromagnetic radiation reflected by the reflector to avoid producing spurious glint reflectors, said variable reflector comprising liquid crystal material in a containment medium, the liquid crystal having an ordinary index of refraction matched to that of the containment medium to transmit said electromagnetic radiation without substantial scattering and an extraordinary index of refraction different from that of the containment medium to cause scattering of said electromagnetic radiation and reflection toward said absorber, and input means for applying a prescribed input to said liquid crystal to switch the same between modes presenting ordinary or extraordinary index of refraction characteristics to said electromagnetic radiation, thereby selectively to permit transmission of said electromagnetic radiation or to reflect said electromagnetic radiation toward said absorber.

18. The system of claim 17, said reflector being oriented in a circle and having plural segments that can be selectively made transmitting or reflecting.

19. A system for controlling electromagnetic radiation, comprising:
an apparatus for responding to electromagnetic radiation, including
a medium through which said electromagnetic radiation may be transmitted;
liquid crystal means positioned with respect to said medium for responding to a characteristic of said electromagnetic radiation to cooperate with said medium to effect refraction of said electromagnetic radiation at an interface of said medium and said liquid crystal means;
a filtering apparatus for filtering a wavelength of said electromagnetic radiation, including a variable polarization rotator means for supplying input electromagnetic radiation at a prescribed angle of polarization, variable dispersion means for rotating the plane of polarization of such input electromagnetic radiation an amount that is a function of the wavelength of such input electromagnetic radiation, and analyzer means for blocking transmission of that electromagnetic radiation which is output by said variable dispersion means and has a plane of polarization which is crossed relative to the axis of polarization of said analyzer means;
control means for activating said filtering apparatus upon said liquid crystal means responding to said characteristic of said electromagnetic radiation; and
wherein said control means comprises a computer and detector means for detecting said reflection and providing a control signal within said control means indicating said refraction is occurring.

20. The system of claim 19, wherein based on said control signal said control means activates said filtering apparatus to filter the wavelength of said electromagnetic radiation having said characteristic.

21. The system of claim 20, further comprising means for resetting said apparatus for responding to permit transmission of said electromagnetic radiation after said filtering apparatus has filtered out said wavelength of electromagnetic radiation having said characteristic.

22. A glint reducing system, comprising:
a variable reflector;
an absorber for receiving electromagnetic radiation reflected by the reflector to avoid producing spurious glint reflections;
said variable reflector comprising,
a liquid crystal material responsive to an electric field to be oriented in accordance with the field, and
containment means having surfaces which affect the orientation of the liquid crystal material in the absence of said field through the interaction between the surfaces and the liquid crystal material, the liquid crystal structure being operative to reduce transmission or to scatter said electromagnetic radiation in the absence of said field and being responsive to the field to increase transmission or to reduce scattering, and
input means for applying said electric field to said liquid crystal material in said variable reflector selectively to permit transmission of said electromagnetic or to reflect said electromagnetic radiation toward said absorber.

23. The system of claim 22, wherein said surfaces are curved.

24. The system of claim 22, wherein said variable reflector is curved.

25. The system of claim 24, wherein said variable reflector is elliptically shaped.

26. A glint reducing system, comprising:
an elliptically shaped variable reflector;
an absorber for receiving electromagnetic radiation reflected by the reflector to avoid producing spurious glint reflections;
said variable reflector comprising,
a liquid crystal material responsive to an electric field to be oriented in accordance with the field, and containment means having curved surfaces which affect the orientation of the liquid crystal material in the absence of said field through the interaction between the curved surfaces and the liquid crystal material, the liquid crystal structure being operative to reduce transmission or to scatter said electromagnetic radiation in the absence of said field and being responsive to the field to increase transmission or to reduce scattering, and input means for applying said electric field to said liquid crystal material in said variable reflector selectively to permit transmission of said electromagnetic radiation or to reflect said electromagnetic radiation toward said absorber.

* * * * *